United States Patent [19]
Bore et al.

[11] 3,971,391
[45] July 27, 1976

[54] PROCESS FOR IMPROVING THE QUALITY OF LIVING, HUMAN HAIR BY LANTHIONIZATION

[75] Inventors: Pierre Bore, Montfermeil; Jean-Claude Arnaud; Grégoire Kalopissis, both of Paris, all of France

[73] Assignee: L'Oreal, Paris, France

[22] Filed: Mar. 8, 1974

[21] Appl. No.: 449,437

[30] Foreign Application Priority Data
  Mar. 8, 1973  Luxemburg ............................ 67178

[52] U.S. Cl. .................................. 132/7; 8/127.51; 424/70; 424/71; 424/72
[51] Int. Cl.² .......................................... A45D 7/06
[58] Field of Search ............. 132/7; 424/71, 72, 70; 8/161, 127.51, 128

[56]  References Cited
  UNITED STATES PATENTS

| | | |
|---|---|---|
| 1,681,170 | 8/1928 | Brown .............................. 424/71 X |
| 1,720,220 | 7/1929 | Kietz et al. ........................ 424/71 X |
| 2,002,989 | 5/1935 | Steinbach ......................... 424/71 X |
| 2,056,358 | 10/1936 | Malone ............................ 424/71 X |
| 2,154,925 | 4/1939 | Wilson ............................ 424/71 X |
| 2,352,524 | 6/1944 | Evans et al. ............................ 8/161 |
| 2,823,168 | 2/1958 | Stonehill ................................ 8/161 |
| 3,154,470 | 10/1964 | Braun et al. ............................ 8/161 |
| 3,331,743 | 7/1967 | Cook ..................................... 424/71 |
| 3,384,548 | 5/1968 | Zviak et al. ............................. 8/161 |

*Primary Examiner*—Albert T. Meyers
*Assistant Examiner*—Vera C. Clarke
*Attorney, Agent, or Firm*—Cushman, Darby & Cushman

[57] ABSTRACT

Process for improving and modifying the cosmetic properties of living human hair comprising transforming about 25 to 70% of the cystine in hair that is not subjected to any extension stress into lanthionine. The process is carried out with an aqueous medium having a pH between about 10.5 and 13 containing at least one alkali or alkaline earth metal hydroxide.

16 Claims, No Drawings

PROCESS FOR IMPROVING THE QUALITY OF LIVING, HUMAN HAIR BY LANTHIONIZATION

BACKGROUND OF THE INVENTION

The present invention has for its object a novel process for improving the qualities or modifying the properties of hair, in particular living human hair, and compositions for treating hair according to this process.

It is already known how to treat textile keratinous fibers to transform at least a part of the cystine into lanthionine.

Such a treatment is performed in a known way on wool but it cannot be used directly to treat living hair.

Applicants have now discovered, in a manner completely surprising, that when a considerable part of the cystine of the hair is transformed into lanthionine, the qualities of the hair are considerably improved and its cosmetic properties modified.

Hair having undergone this transformation called lanthionization has a different composition and structure from that of normal hair, which gives it interesting new properties.

Thus, lanthionized hair shows a great elasticity when it is in the wet state.

This property is manifested more particularly when lanthionized hair is subjected to combing in the wet state, for example, after shampooing. Then it has been found that lanthionized hair is much more resistant to breaking and that the number of hairs broken during such an operation is clearly less than that of natural hairs, i.e., unlanthionized.

Thus, when, for example, about 70% of the cystine was transformed into lanthionine by the process according to the invention, the number of hairs broken in the wet state was less than half the number of hairs broken in the case of natural hairs.

Further, it has been found that hair subjected to a lanthionization presents a holding after setting which is clearly improved.

Thus, if previously lanthionized hair is set and this setting is compared with that of hair not treated according to the invention, it is found that the holding of the setting is clearly higher in the case of lanthionized hair, in an atmosphere of normal relative humidity, i.e., between about 50 and 70%.

This property is more marked the greater the percentage of cystine transformed into lanthionine.

This characteristic of lanthionized hair means that, after setting, this hair, in an atmosphere of normal relative humidity, resumes its initial form less rapidly than untreated hair.

It has also been found that hair subjected to lanthionization according to the process of the invention presents a greater permeability to the hair treating agents than untreated hair. This improved permeability generally facilitates all capillary treatments, in particular dyeing operations, whether direct dyeing or oxidation dyeing is involved, and bleaching operations. Thus dyeing and bleaching are realized more easily and rapidly than in the case of untreated hair and, in addition, the intensity of the coloring is improved. Further, in treating lanthionized hair with standard capillary products intended to give the hair more suppleness or brilliance, better results are obtained than in the case where the same treatment is applied to unlanthionized hair.

It has also been found that hair, of which a considerable part of the cystine has been transformed into lanthionine, presents an alkaline solubility less than that of natural hair not treated according to the invention. By alkaline solubility is meant the loss of weight by putting in the presence of an N/4 sodium hydroxide solution at a temperature of 65°C.

It should be noted that lanthionization of hair gives it irreversible properties which it keeps during its entire life. This is particularly the case for better holding of a setting which is retained for all successive settings, without it being necessary to use any additional product, even if these later settings are simply done with water.

When the hair is not subjected, during treatment, to any extension, it is necessary, to obtain an interesting improvement of the cosmetic qualities of the hair to transform about 25 to 70% and preferably 35 to 70% of cystine into lanthionine.

To achieve this result, according to the invention, the lanthionization of the hair can be performed by treating the hair in an aqueous medium with a composition having a pH between about 10.5 and 13, for a sufficient time to obtain the desired proportion of lanthionine, keeping the hair in the wet state during the entire treatment.

The compositions having a pH of 10.5 to 13, which can be used for putting into practice the above process, are particularly compositions with a base of alkaline earth or alkali metal hydroxides, whose concentration is a function of the desired pH value.

In the case where the process of the invention is used to treat live hair, not subjecting it to any extension stress, the above process should be practiced at a sufficiently high temperature so that the treatment period is not too long; however, this temperature should be bearable under a heating hood, i.e., it should not exceed 50°C.

Preferably the treatment temperature is between about 25° and 50°C.

The period of treatment, which is a function of the proportion of lanthionine desired, varies according to treatment condition, and particularly according to the composition used and the temperature, as will be explained in detail below.

Therefore, theoretically the period of treatment can vary from a few minutes to a few hours, but, for practical reasons, the characteristics of the process of the present invention have been selected so that the treatment period is not less than 10 minutes or greater than about 60 minutes.

It should be noted that when the composition is a simple aqueous solution of alkaline base, the treatment time should be longer than in the case of a composition in gel or cream form, if it is desired to obtain a comparable degree of lanthionization.

Of course, it is necessary to rinse carefully the hair after treatment.

The proportion of lanthionization which is obtained with the treatment according to the invention (i.e., the percentage of cystine which is transformed into lanthionine) depends on the different characteristics of the treatment.

Thus, the proportion of lanthionization is higher the higher the pH of the composition according to the invention.

The increase of temperature also plays a role in the sense of an increase of the degree of lanthionization.

The influence of these different variables will be illustrated below with concrete examples.

It has also been noted that when the alkaline composition according to the process of the invention is applied to dry hair, the degree of lanthionization is generally higher than when the same composition is applied, under the same conditions, but to hair previously wetted. In case it is possible to apply the composition to dry hair, this makes it possible to apply the process of the invention, lowering either the pH of the composition or the temperature of the treatment period.

According to the invention, an effort should not be made to exceed a degree of lanthionization of 70% which seems to constitute an optimal result for natural hair, i.e., not having previously undergone permanent deformation treatment or bleaching, otherwise the hair is degraded without increasing its degree of lanthionization.

On the other hand, when hair is to be treated that has been previously degraded by prior capillary treatments, i.e., hair whose relative proportion of cystine is less than the normal content by at least about 10%, in this case, the degree of lanthionization applied according to the process of the invention should be reduced correspondingly.

To do this, the period or temperature of treatment or the pH of the composition should be reduced. For example, it would be possible to use compositions having a pH of 10.5 to 12, at a temperature between 25° to 30°C and 50°C for a period between 5 and 20 to 30 minutes.

According to a first embodiment of the invention, the hair is treated in an aqueous medium with a composition of a base of alkaline earth or alkali metal hydroxide having a pH between 12.5 and 13, at a temperature between 40° and 50°C, for a sufficient time to obtain the desired degree of lanthionine, this time being between 10 and 60 minutes. This time generally varies between 20 and 60 minutes in the case where the composition is a simple aqueous solution with an alkaline base.

To maintain the hair in a wet state during treatment, it is possible, for example, to cover the hair with an impermeable cap preventing the loss of water by evaporation.

The nature of the hydroxide giving the composition its pH between about 12.5 and 13 does not have a critical influence on the treatment according to the invention. For example, it is possible to use the following hydroxides: $Ca(OH)_2$, LiOH, NaOH, KOH, or their mixtures, without this list being limiting.

The molar concentration of the alkali or alkaline-earth metal hydroxides or their mixtures in the composition is determined by the desired value of the pH of the composition which should be between 12.5 and 13.

When operating according to the first embodiment of the invention, at about 40°C, the treatment period is generally of the order of 20 to 60 minutes. However, if the composition is a simple aqueous solution with an alkaline base, the treatment period should be at least about 40 minutes.

When operating, according to the first embodiment of the invention, at about 50°C, the treatment period is generally of the order of 10 to 60 minutes (20 to 60 minutes in the case of an aqueous solution).

To illustrate more concretely the influence of temperature and the treatment period, there are given below the results obtained by treating hair with an 0.1 N sodium hydroxide solution (pH = 13). The results are summarized in the following table.

| Temperature in °C | Time in Minutes | Degree of lanthionization in % |
|---|---|---|
| 40 | 40 | 25 |
|  | 60 | 29 |
| 50 | 20 | 27 |
|  | 30 | 40 |
|  | 60 | 51 |

According to a second embodiment of the invention, it is also possible to perform the lanthionization treatment with compositions with an alkaline-earth or alkali metal hydroxide base, but, in addition, comprising particular substances which have the effect of making it possible to reduce the time, temperature and/or pH of the treatment. Hereafter these substances will be designated as "lanthionization activators."

According to this second embodiment, the hair is treated in an aqueous medium with a composition of alkali or alkaline-earth metal hydroxide base having a pH between about 10.5 and 13, at a temperature between 25° and 50°C, for a sufficient period to obtain the desired degree of lanthionization, this period being around 10 to 60 minutes, said composition containing, in addition, a lanthionization activator selected from the group consisting of electrolytes that are neutral from an oxidation-reduction viewpoint, reducing agents have a limited hydrolytic action on the S-S bonds of the cystine, and cationic surfactants.

The alkali or alkaline-earth metal hydroxides that can be used in the second embodiment of the process of the invention are particularly $Ca(OH)_2$, LiOH, NaOH, KOH, or their mixtures. Their concentration is a function of the desired value of the pH which should be between 10.5 and 13.

The neutral electrolytes from the oxidation-reduction viewpoint can be inorganic electrolytes, such as alkali metal halides such as, for example, sodium chloride, or lithium bromide, or alkaline-earth metal halides such as calcium chloride, or again alkali or alkaline-earth metal sulfates such as sodium, potassium or calcium sulfate.

Preferably, they are used in a concentration up to 5 moles per liter.

The electrolytes, neutral from an oxidation-reduction viewpoint, can also be organic electrolytes such as guanidine carbonate, and can preferably be used in a concentration up to one mole per liter.

The reducing agents having a limited hydrolytic action on the S-S bonds of the cystine can be made up for example, of alkali or alkaline-earth metal sulfides, in a concentration of up to $3 \times 10^{-2}$ moles per liter, or again of alkali or alkaline-earth metal sulfites in a concentration between $10^{-3}$ and $10^{-1}$ moles per liter.

The activators, made up of cationic surface active compounds, can be made up, for example, of cetyl trimethylammonium bromide (known under the trademark Cetavlon) in a concentration of up to $3 \times 10^{-2}$ moles per liter, or a quaternary ammonium hydroxide such as that known as Hyamine 10 X, in a concentration of up to $10^{-1}$ moles per liter.

It should be noted that according to the second embodiment of the process of the invention, treatment of the hair can be performed either without heating, i.e., in practice, at about 25°–40°C, or with heating between 40 and 50°C. In this latter case, the heating is obtained under a heating hood, the hair being covered with an impermeable cap to prevent any loss of water.

The operating condition of the treatment according to the second embodiment of the invention, as a function of the temperature at which it is desired to operate, can be made precise as indicated below.

When operating between 25° and 40°C, the treatment period is generally of the order of 30 and 60 minutes.

When operating between 40° and 50°C, the treatment period is generally of the order of 10 to 60 minutes.

To illustrate more concretely the influence of temperature and the treatment period and the influence of the presence of a lanthionization activator, there are given below the results obtained by treating hair with a 0.1 N sodium hydroxide solution, to which has been added lithium bromide so that the LiBr concentration is between 0.1 M and 3.8 M, which has the effect of making the pH vary from 12.8 to 10.5. The results are summarized in the following table.

ethers such as nonylphenol polyethoxyethers; fatty acids such as oleic acid; fatty alcohols such as oleyl alcohol; hydroxyethyl cellulose, and the like.

It should be noted that according to the invention the alkaline composition which makes it possible to achieve the transformation of cystine into lanthionine should be without alcohol or with a slight alcohol content (preferably less than 10%) because the presence of alcohol increases the alkaline solubility of the hair.

The treatment according to the invention is clearly distinguished from standard processes of hair treatment such as those which are used for permanent deformations, oxidizing dyeings, or bleachings, because these treatments are always carried out under conditions different from those according to the invention, and they practically always take place in a medium that is both alkaline and oxidizing.

At the time of these standard treatments, it seems that a certain amount of keratocystine (K-S-S-K) is temporarily transformed into lanthionine (K-S-K), but since the nascent lanthionine is very sensitive to oxidizing agents (peroxide, persulfate, etc.) it immediately

| Temperature in °C | Time in minutes | Degree of lanthionization in % | | | | |
|---|---|---|---|---|---|---|
| | | pH 10.5 | pH 11 | pH 11.5 | pH 12 | pH 12.8 |
| 25 | 40 | | | | | 27 |
| | 50 | | | | 25 | |
| | 60 | 29 | | | 35 | 38 |
| 40 | 30 | | 25 | | 25 | 28 |
| | 50 | 25 | | | | |
| | 60 | 30 | | | 45 | 48 |
| 50 | 10 | 35 | 36 | 36 | | 37 |
| | 20 | | 50 | | | 45 |
| | 30 | 47 | | | | |
| | 60 | 53 | 65 | 55 | | 55 |

The present invention also has for its object the novel industrial product made up of a composition for treating hair according to the process defined above, said composition being characterized by the fact that it has a pH between about 10.5 and 13, and that it contains in an aqueous medium at least an alkali or alkaline-earth metal hydroxide and at least a lanthionization activator selected from the group consisting of electrolytes, neutral from an oxidation-reduction viewpoint, inorganic or organic, reducing agents having a limited hydrolytic action on the S-S bonds of the cystine, and cationic surfactant compounds.

The lanthionization activators are present in amounts as indicated above in the compositions of the invention.

The compositions used according to the invention are advantageously in gel or cream form, with sufficient consistency for the composition to be retained naturally on the hair. In this way, there is prevented a considerable evaporation of the aqueous phase which should subsist to assure practice of the process according to the invention. Actually, according to the invention, it is necessary that the hair be kept in the wet state during the entire treatment period.

Further, the cream or gel should be such that the aqueous phase containing the active substances can come in contact and assure impregnation of the hair.

These emulsions constituting the composition are preferably of the oil in water type.

The compositions according to the present invention are prepared according to the usual methods.

They comprise adjuvants usually used in creams or gels, particularly, polyoxyethylene glycols; other polygives rise to the formation of oxides corresponding to the formula K-SO-K and K-SOO-K, K being the residue of the keratinous molecule.

Such a transformation is irreversible and at the time of hydrochloric hydrolysis of hair treated by standard processes, comprising such oxides, these latter decompose to give cysteic acid ($KSO_3^-$).

On the other hand, when hair is treated according to the invention a considerable formation of lanthionine is obtained which is stable in regard both to alkaline and acid agents.

Hair treated according to the invention shows, after having undergone a hydrochloric hydrolysis, a degree of lanthionine which remains unchanged and which is always reproducible under precise dosing conditions.

There is indicated below the way to determine the degree of lanthionization under consideration in the present application.

DEFINITION OF DEGREE OF LANTHIONIZATION

The degree is equal to the percentage of initial cystine bonds of the natural hair transformed into lanthionine bonds during the treatment.

TECHNIQUE OF ANALYSIS OF THE HAIR PRINCIPLE

The different amino acids are separated by chromatography on a sulfonic-type ion exchange resin after hydrochloric hydrolysis, followed by a ninhydrin colorimetery and a quantitative determination in relation to a standard.

EQUIPMENT

Technicon TSM 1 autoanalyser
Technique: according to the Technicon methodology
Elution buffers: sodium citrate
Buffer 1 pH 3.25 0.2N Na⁺ 0.1 M citrate 6% methanol
Buffer 2 pH 3.15 0.2N Na⁺ 0.1 M citrate 6% methanol
Buffer 3 pH 4.25 0.2N Na⁺ 0.1 M citrate 6% methanol
Buffer 4 pH 6.00 0.37 N 0.1 M citrate 6% methanol

MODE OF OPERATION 20 mg of dry hair (dried at 120° for 20 minutes) are carefully weighed.

The hair is hydrolyzed with 5 ml of 5.6 N (azeotrope) hydrochloric acid in a sealed test tube. It is left in an oven at 120°C for 4 hours with agitation.

The tube is opened and the hydrolysate is brought to dryness in a rotary evaporator at 35°C under vacuum. The residue is dissolved with 10 ml of distilled water and again dried.

10 ml are quantitatively transferred with decinormal hydrochloric acid into a graduated flask. 0.1 ml is deposited in 2 shallow dishes.

A control deposit of 0.05 ml is made, in two shallow dishes, of the standard solution containing 2.5 moles per ml of each amino acid and in particular lanthionine.

CALCULATIONS

1. Surfaces S and S standard are noted on the chromatograms obtained respectively with the hydrolysate of hair and with the standard solution for the batches of each amino acid.
2. For each amino acid there is calculated $$K = \frac{0.0125\ S \times MW}{S_{st} \times Sa}$$

a formula wherein

K represents the amount (in g) of each amino acid present in 100 g of hair.

MW is the molecular weight of the amino acid considered.

Sa is the sampling in mg of hair.

3. Degree of lanthionization

The amount of cystine present in the average undegraded hair is 16%.

Degree of lanthionization: L = K lanthionine × 7.2.

For a better understanding of the invention there will now be described a way of illustration and without any limiting character several examples of embodiment.

First, there will be defined a method of application which can be used to embody the invention by using the compositions which are described below by way of example.

Method of application of treatment (hair not subjected to an extension)

The composition according to the invention (gel or cream) is applied with a brush. Each lock is treated separately starting from the roots and going to the tip. After all the hair is thoroughly coated, it is covered with a plastic cap to prevent any loss of water during heating (because the formation of lanthionine is hydrolysis of the keratocystine). Heating is performed under a hood during a period to be determined, depending on the formula applied.

Then a thorough rinsing is performed, followed by a gentle shampoo.

The hair is then set with water or any other aqueous solution in the usual way.

Examples are given below of compositions and treatment which can be realized according to the method of application just defined. These examples are given solely by way of illustration.

In these examples are indicated the degree of lanthionization obtained and, in certain cases, the improvement of the holding of the setting.

The rate of lanthionization was determined as indicated above.

Improvement of the holding of the setting can be determined by the following process:

DETERMINATION OF THE IMPROVEMENT OF THE HOLDING OF THE SETTING

Definition: Improvement of the holding of a lock of treated hair after wetting and drying on rollers, subjected to a release under the action of its own weight in an atmosphere of fixed relative humidity (65%) for 2 hours at 22°C, in relation to a lock of natural hair.

TECHNIQUE

Equipment

Plastic box (35 × 45 × 30 cm) provided with a small fan permitting homogenization, with opening in the lid.

The relative humidity set at 65% is obtained with a saturated solution of sodium nitrite.

MODE OF OPERATION

Locks of 800 mg and about 240 mm of useful length are wetted by dipping in a beaker of 250 ml of distilled water, then rolled on rollers 2 cm in diameter.

Drying is for 2 hours in an oven at 60°C.

After cooling at ambient temperature, the locks are removed from the rollers and suspended by small clips on the inside of the measuring enclosure.

The uncurling is followed by watching the end of the locks which uncurl in front of a stiff sheet of paper marked off in millimeters. Each series of measurements is made in comparison with a control lock (untreated natural hair).

Readings are made every 5 minutes for 2 hours and 30 minutes. A final reading is made after 16 hours.

CALCULATIONS

Improvement of the holding of the setting is given by the formula $$T = \frac{l_c - l_x}{l - l_c} \times 100$$

wherein:

$l_c$ is the length of the control lock after 2 hours uncurling $l_x$ is the length of the treated lock after 2 hours uncurling $l$ is the length of the lock at rest ($\approx$ 240 mm).

EXAMPLE 1

| Formula: | Gel | |
|---|---|---|
| | Hydroxyethyl cellulose WP 4400 | 4 g |
| | Hydrated lithium oxide (LiOH,H₂O) | 2 g |
| | Lithium bromide (LiBr) | 26 g |
| | Water sufficient for | 100 g |
| pH gel: | 11 | |
| Use: | | |
| | Temperature: 25°C | |

-continued time: 60 minutes

Degree of lanthionization (application to dry hair): 29% Improvement of the holding of the setting: +33%

EXAMPLE 2

Formula: Gel
- Hydroxyethyl cellulose WP 4400 — 4 g
- Hydrated lithium oxide (LiOH,H$_2$O) — 1.5 g
- Sodium sulfite (Na$_2$SO$_3$) — 0.62 g
- Water sufficient for — 100 g pH gel: 12.3
Use:
- Temperature: 35°C
- time: 40 minutes Degree of lanthionization (application to dry hair): 25%

EXAMPLE 3

Formula: Gel
- Hydroxyethyl cellulose WP 4400 — 4 g
- Sodium hydroxide (NaOH) — 4 g
- Water sufficient for — 100 g pH gel: 12.9
Use:
- Temperature: 40°C
- time: 30 minutes Degree of lanthionization (application to wet hair): 56.5% Improvement of the holding of the setting: +65%

EXAMPLE 4

Formula: Gel
- Hydroxyethyl cellulose WP 4400 — 4 g
- Hydrated lithium oxide (LiOH,H$_2$O) — 2 g
- Water sufficient for — 100 g pH gel: 12.6
Use:
- Temperature: 40°C
- time: 20 minutes Degree of lanthionization on dry hair: 26%

EXAMPLE 5

Formula: Gel
- Hydroxyethyl cellulose WP 4400 — 4 g
- 60% strontium sulfide (SrS) — 0.36 g
- Sodium hydroxide (NaOH) — 1.6 g
- Water sufficient for — 100 g pH gel: 12.8
Use:
1) temperature: 40°C
   time: 35 minutes
Degree of lanthionization on dry hair: 26%
2) temperature: 40°C
   time: 50 minutes
Degree of lanthionization on wet hair: 25%

EXAMPLE 6

Formula: Gel
- Hydroxyethyl cellulose WP 4400 — 4 g
- Sodium hydroxide (NaOH) — 2 g
- Lithium bromide (LiBr) — 3.9 g
- Water sufficient for — 100 g pH gel: 12.3
Use:
- Temperature: 40°C
- time: 45 minutes Degree of lanthionization on dry hair: 44.5%

EXAMPLE 7

Formula: Gel
- Hydroxyethyl cellulose WP 4400 — 4 g
- Hydrated lithium oxide (LiOH,H$_2$O) — 2 g
- Lithium bromide (LiBr) — 34.8 g
- Water sufficient for — 100 g pH gel: 10.5
Use:
- temperature: 45°C
- time: 15 minutes Degree of lanthionization on dry hair: 37%
Improvement of holding of setting: +40%

EXAMPLE 8

Formula: Cream
- 40% potassium laurate — 52 g
- Hydrated lithium oxide (LiOH,H$_2$O) — 1 g
- Lithium bromide (LiBr) — 26 g
- Water sufficient for — 100 g pH cream: 11
Use:
- Temperature: 45°C
- time: 15 minutes Degree of lanthionization on dry hair: 38%

EXAMPLE 9

Formula: Gel
- Hydroxyethyl cellulose WP 4400 — 4 g
- Hydrated lithium oxide (LiOH,H$_2$O) — 2 g
- Sodium chloride (NaCl) — 17.5 g
- Water sufficient for — 100 g pH gel: 11.7
Use:
- Temperature: 45°C
- time: 15 minutes Degree of lanthionization on dry hair: 35%
Improvement of the holding of the setting: +27%

EXAMPLE 10

Formula: Gel
- Hydroxyethyl cellulose WP 4400 — 4 g
- Hydrated lithium oxide (LiOH,H$_2$O) — 2 g
- Potassium sulfate (K$_2$SO$_4$) — 17.4 g
- Water sufficient for — 100 g pH gel: 12.7
Use:
- Temperature: 45°C
- time: 15 Minutes Degree of lanthionization on dry hair: 42.5%
Improvement of the holding of the setting: +38%

EXAMPLE 11

Formula: Gel
- Hydroxyethyl cellulose WP 4400 — 4 g
- Hydrated lithium oxide (LiOH,H$_2$O) — 2 g
- Lithium bromide (LiBr) — 26 g
- Water sufficient for — 100 g pH gel: 11
Use:
- Temperature: 45°C
- time: 20 minutes Degree of lanthionization on dry hair: 52.5%
Improvement of holding of setting: +50%

EXAMPLE 12

Formula: Cream
- Hydroxyethyl cellulose WP 4400 — 4 g
- Hydrated lithium oxide (LiOH,H$_2$O) — 2 g
- Calcium sulfate (CaSO$_4$) — 10.2 g
- Water sufficient for — 100 g pH cream: 12.4

-continued

Use:
    Temperature: 50°C
    time: 10 minutes
Degree of lanthionization on dry hair: 28%
Improvement of holding of setting: +18%

EXAMPLE 13

Formula:  Gel
    Hydroxyethyl cellulose WP 4400      4 g
    Sodium hydroxide (NaOH)             2.4 g
    Water sufficient for                100 g
pH gel: 12.8
Use:
    Temperature: 50°C
    time: 30 minutes
Degree of lanthionization on wet hair: 48%
Improvement of the holding of the setting: +51%

EXAMPLE 14

Formula:  Gel
    Hydroxyethyl cellulose WP 4400      4 g
    Hydrated lithium oxide (LiOH,H$_2$O)   2 g
    Cetavlon                            10 g
    Water sufficient for                100 g
pH gel: 12.4
Use:
    Temperature: 50°C
    time: 35 minutes
Degree of lanthionization on dry hair: 30%

EXAMPLE 15

Formula:  Cream
    Nonylphenol polyethoxyether (n=4)   12 g
    Nonylphenol polyethoxyether (n=8)   10 g
    Oleic acid                          3 g
    Triethanolamine                     7 g
    Oleyl alcohol                       8 g
    Ethanol                             10 g
    Calcium oxide (CaO)                 12.5 g
    Water sufficient for                100 g
pH cream: 12.7
Use:
    Temperature: 50°C
    time: 40 minutes
Degree of lanthionization on wet hair: 44%

EXAMPLE 16

Formula:  Gel
    Hydroxyethyl cellulose WP 4400      4 g
    Sodium hydroxide (NaOH)             2 g
    Lithium bromide (LiBr)              26 g
    Cetavlon                            5 g
    Water sufficient for                100 g
pH gel: 11.2
Use:
    Temperature: 50°C
    time: 50 minutes
Degree of lanthionization on wet hair: 45%

EXAMPLE 17

Formula:  Gel
    Hydroxyethyl cellulose WP 4400      4 g
    Guanidine carbonate                 18 g
    Hydrated lithium oxide (LiOH,H$_2$O)   2 g
    Water sufficient for                100 g
pH gel: 12.7
Use:
    Temperature: 50°C
    time: 50 minutes
Degree of lanthionization on dry hair: 58%
Degree of lanthionization on wet hair: 44%

What is claimed is:

1. A process for improving and modifying the cosmetic properties of living human hair comprising thoroughly coating said hair, which is not subjected to any extension stress, with a composition consisting essentially of an aqueous medium of an alkali or alkaline earth metal hydroxide present in an amount effective to impart to the composition a pH ranging from 12.5 to 13, and heating said hair at a temperature between 40°–50°C, while maintaining said hair in the wet state, for a period of time effective to convert about 25 to 70 percent of the cystine in said hair to lanthionine.

2. The process of claim 1 wherein about 35 to 70% of the cystine is converted to lanthionine.

3. The process of claim 1 wherein the hair is heated for about 10 to 60 minutes.

4. The process of claim 3 wherein the hair is heated at about 40°C for from 20 to 60 minutes.

5. The process of claim 3 wherein the hair is heated at about 50°C for from about 10 to 60 minutes.

6. The process of claim 1 wherein said alkali or alkaline earth metal hydroxide is calcium hydroxide, lithium hydroxide, sodium hydroxide or potassium hydroxide.

7. The process of claim 1 wherein said hair is heated at a temperature between about 40° and 50°C by placing the hair thoroughly coated with said composition in a heating means consisting of a hood.

8. The process of claim 1 wherein the composition is an oil-in-water emulsion.

9. A process for improving the cosmetic properties of living human hair comprising applying to said hair, which is not subjected to any extension stress, in an amount effective to impregnate said hair, a composition consisting essentially of a mixture, in an aqueous medium, of (1) an alkali or alkaline earth metal hydroxide present in an amount effective to impart to said composition a pH ranging from about 10.5 to 13, and 2. a lanthionization activator selected from the group consisting of
   a. an inorganic neutral electrolyte present in an amount up to 5 moles per liter,
   b. an organic neutral electrolyte present in an amount up to 1 mole per liter,
   c. an alkali or alkaline earth metal sulfide present in an amount up to $3 \times 10^{-2}$ mole per liter,
   d. an alkali or alkaline earth metal sulfite present in an amount ranging from $10^{-3}$ to $10^{-1}$ mole per liter and
   e. cetyl trimethylammonium bromide present in an amount up to $3 \times 10^{-2}$ mole per liter, and
heating said hair, impregnated with said composition, at a temperature between 25° and 50°C, while maintaining said hair in the wet state, for a time effective to convert about 25 to 70 percent of the cystine in said hair to lanthionine.

10. The process of claim 9 wherein said hair is heated at a temperature between about 25° and 40°C for from about 30 to 60 minutes.

11. The process of claim 9 wherein said hair is heated at a temperature between about 40° and 50°C for from about 10 to 60 minutes.

12. The process of claim 9 wherein said hair is heated for about 10 to 60 minutes.

13. The process of claim 9 wherein said alkali or alkaline earth metal hydroxide is calcium hydroxide, lithium hydroxide, sodium hydroxide or potassium hydroxide.

14. The process of claim 9 wherein said hair is heated to a temperature between about 40° to 50°C under a hood.

15. The process of claim 9 wherein said composition comprises an oil-in-water emulsion.

16. A process for improving and modifying the cosmetic properties of degraded living human hair having a cystine content of at least 10 percent less than the cystine content of normal hair comprising thoroughly coating said degraded hair, which is not subjected to any extension stress, with a composition consisting essentially of an aqueous medium of an alkali or alkaline earth metal hydroxide present in an amount effective to impart to said composition a pH ranging from 10.5 to 12, and heating said hair at a temperature between 25° and 50°C for a period between 5 and 30 minutes while maintaining the hair in the wet state during said period.

* * * * *